United States Patent [19]

Tóth et al.

[11] Patent Number: 4,868,184
[45] Date of Patent: Sep. 19, 1989

[54] BENZHYDRYLPIPERAZINES PHARMACEUTICAL COMPOSITIONS THEREOF AND METHOD OF USE

[75] Inventors: Edith Tóth, Budapest; Béla Kiss, Vecsés; József Törley, Budapest; Éva Pálosi, Budapest; István Hajdu, Budapest; László Szporny, Budapest; Dóra Gróó, Budapest; Erzsébet Lapis, Budapest; István Laszlovszky, Budapest, all of Hungary

[73] Assignee: Richter Gedeon Vegyeszeti Gyar, Budapest, Hungary

[21] Appl. No.: 41,233

[22] Filed: Apr. 22, 1987

[30] Foreign Application Priority Data

Apr. 28, 1986 [HU] Hungary .................. 2251/1751/86

[51] Int. Cl.$^4$ .................. A61K 31/495; C07D 295/08
[52] U.S. Cl. .................................... 514/255; 544/397
[58] Field of Search .................... 544/397; 514/255

[56] References Cited

U.S. PATENT DOCUMENTS

| | | | |
|---|---|---|---|
| 2,603,435 | 3/1953 | Baltzly et al. | 544/396 |
| 2,709,169 | 5/1955 | Morren | 544/396 |
| 2,861,072 | 11/1958 | Weston et al. | 544/396 |
| 2,899,436 | 8/1959 | Morren | 544/396 |
| 3,178,422 | 4/1965 | Cusic et al. | 540/575 |
| 3,652,568 | 3/1972 | Winter et al. | 544/397 |
| 4,265,894 | 5/1981 | Gootjes | 514/255 |

FOREIGN PATENT DOCUMENTS

| | | | |
|---|---|---|---|
| 1062248 | 7/1959 | Netherlands | 544/397 |
| 92790 | 9/1958 | Norway | 544/397 |
| 837986 | 6/1960 | United Kingdom | 544/397 |

OTHER PUBLICATIONS

Carlsson, (1988), Perspectives in Psychopharmacology Collection of Papers in Honor of E. Usdin. Alan L. Riss, Inc., pp. 209-223.
Gottries, (1985), Psychopharmacology, 86:245-252.
Morren, N-Monobenzhydrylpiperazines, CA: vol. 53, 18071i-18073c, (1959), eq. BE 523899-523903.
Janssen, Pharmacologically Active Piperazine Derivatives, CA, vol. 54, 2379b, (1960), eq. UK 809760.
UCB, Societe Anon., N-Benzhydrylpiperazine Derivatives, CA, vol. 64, 8207f, (1966), eq. BE 649848.
Nakanishi et al., Piperazine Derivatives, CA, vol. 81, 91580a, (1974), eq. JP 7411713.
Buzas et al., [(Benzhydrloxy)alkyl]piperazines, CA, vol. 88, 62416r, (1978).
Abbott Laboratories, N-Diarylmethylpiperazines, CA, vol. 51, 5847a; 1957.
Walter et al., Unsymmetrically Substituted Piperazines, CA, vol. 53, 21986f-21987f, (1959).
Barrett et al., CA; vol. 57, 13778d, Piperazine Derivatives.

*Primary Examiner*—Cecilia Shen
*Attorney, Agent, or Firm*—Keil & Weinkauf

[57] ABSTRACT

The invention relates to novel benzhydryl-piperazine derivatives of the general formula (I) and the acid addition and quaternary ammonium salts thereof, pharmaceutical compositions containing them and a process for their preparation. In the general formula (I)

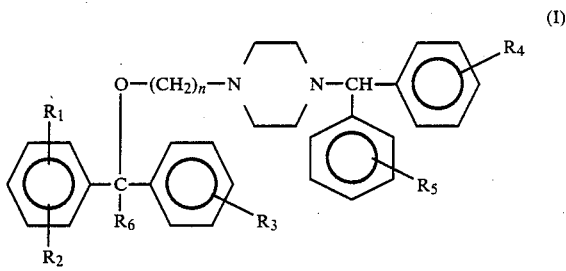

$R_1$, $R_2$, $R_3$, $R_4$ and $R_5$ are the same or different and stand for hydrogen or halogen, or a trihalomethyl, $C_{1-4}$ alkyl or $C_{1-4}$ alkoxy group;
  $R_6$ means hydrogen or a $C_{1-4}$ alkyl group; and
  n is 2 or 3.

The compounds of the general formula (I) are useful for treating diseases arising from a decrease in the dopamine level, i.e. from a hypofunction of the dopaminergic system, and have low toxicity.

5 Claims, No Drawings

BENZHYDRYLPIPERAZINES PHARMACEUTICAL COMPOSITIONS THEREOF AND METHOD OF USE

The invention relates to therapeutically useful novel benzhydrylpiperazine derivatives of the general formula (I),

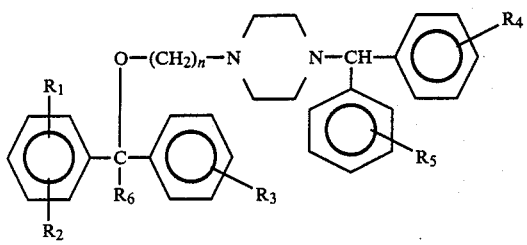

wherein
$R_1$, $R_2$, $R_3$, $R_4$ and $R_5$ are the same or different and stand for hydrogen or halogen, or a trihalomethyl, $C_{1-4}$ alkyl or $C_{1-4}$ alkoxy group;
$R_6$ means hydrogen or a $C_{1-4}$ alkyl group; and n is 2 or 3, as well as their pharmaceutically acceptable acid addition and quaternary ammonium salts and pharmaceutical preparations containing these compounds.

According to an other aspect of the invention, there is provided a process for the preparation of the new compounds of the general formula (I) and acid addition as well as quaternary ammonium salts thereof.

The compounds of the general formula (I) may contain one or more asymmetric carbon atoms and thus they may exist in various stereoisomeric forms. Therefore, the compounds of the general formula (I) may be bases, acid addition salts, quaternary ammonium salts, racemates, separated optical isomers and the mixtures thereof as well as the solvates, e.g. hydrates, of these compounds.

Several therapeutically useful 1,4-disubstituted piperazine derivatives have been described in the literature, wherein one nitrogen atom of the piperazine ring is substituted by a benzhydryl or a benzhydryloxyalkyl group, whereas most various groups are bond to the other nitrogen atom. Such compounds are described e.g. in the Belgian patent specifications Nos. 523,899; 523,900; 523,901; 523,902; 523,903, and 649,848, in the published Dutch patent application No. 8,202,636, in the published British patent application No. 809,760, in the published German patent applications Nos. 2,719,246 and 2,755,752, in the published Japanese patent application Nos. 7,411,713, in the published South-African patent application No. 6,906,642 and in the U.S. Pat. No. 3,178,422.

The difference between the compounds of the general formula (I) of the invention and the known compounds is that the compounds of the general formula (I) contain both the benzhydryl and benzhydryloxyalkyl groups within the same molecule; up to the present, no compound of such type has been reported in the literature.

The novel compounds of the general formula (I) and their pharmaceutically acceptable salts show a strong, selective dopaminergic activity on the central nervous system and thus they are useful for treating diseases occurring as a consequence of the degeneration and/or hypofunction of the dopaminergic system, such as depression, parkinsonism, several neuroendocrine illnesses, "ageing", impotence and the like.

The dopaminergic activity of the compounds of the invention and their salts was determined by in vitro and in vivo animal tests.

(a) Measurement of the modification of the locomotor activity

The hypermotivity induced by L-DOPA [L-(3,4-dihydroxyphenyl)-α-alanine] is influenced by dopaminergic substances. The method of N. P. Plotnikoff et al. ["The Thyroid Axis, Drugs and Behavior", Raven Press N.Y., pp. 103–113 (1974)] was used for this study.

Male Hann-Wistar rats weighing 160 to 180 g were used. Animal groups of 5 members each were intraperitoneally (i.p.) treated with 40 mg/kg of body-weight (abbreviated: mg/kg) of pargyline [N-methyl-N-(2-propynyl)-benzylamine] and after 60 minutes, the compounds to be tested were orally given in a dose of 30 mg/kg as an 0.5% Tween suspension. The control groups were treated with placebo (i.e. with 10 mg/kg of an aqueous solution containing 0.5% of Tween in distilled water). Thirty minutes later, 100 mg/kg of L-DOPA were intraperitoneally administered. The locomotor activity of the animals was registered by using a 5-channel VKI (Type UPAMS-01) motimeter for 3 hours following the treatment. (In the course of the measurement, the time of the active movement of the animals was registered.) The results are given as the percentage of the control in Table 1.

In the Tables, the following abbbreviations are used:
n: number of the animals
i.p.: intraperitoneal(ly)
p.o.: oral(ly)
L-DOPA: [L-(3,4-dihydroxyphenyl)-α-alanine]
$\bar{x} \pm SE$: average+stanard error
The following compounds are listed in the Tables.

A: 1-[3-[bis(4-fluorophenyl)methoxy]propyl]-4-[bis(4--fluorophenyl)methyl]piperazine B: 1-[3-[(4-methoxyphenyl)-(3-trifluoromethylphenyl)methoxy]propyl]-4-[(4-methoxyphenyl)-(3-trifluoromethylphenyl)methyl]piperazine C: 1-[3-[bis(4-fluorophenyl)methoxy]propyl]-4-[(2-chlorophenyl)-(4-fluorophenyl)methyl]piperazine D: 1-[3-(diphenylmethoxy)propyl]-4-[(2-chlorophenyl)-(4-fluorophenyl)methyl]piperazine E: 1-[2-[bis(4-fluorophenyl)methoxy]ethyl]-4--diphenylmethylpiperazine F: 1-[3-[bis(4-fluorophenyl)methoxy]propyl]-4-[(4-fluorophenyl)phenylmethyl]piperazine G: 1-[3-(diphenylmethoxy)propyl]-4-[bis(4-fluorophenyl)methyl]piperazine H: 1-[3-(diphenylmethoxy)propyl]-4-[(4-fluorophenyl)-phenylmethyl]piperazine.

The compound B was used as dimaleate; the other compounds were investigated as dihydrochlorides.

TABLE 1

| Compound | Dose mg/kg p.o. | Locomotor activity total movements/3 hours as percentage of the control | n |
|---|---|---|---|
| A | 30 | 158 ± 8.8 | 15 |
| B | 30 | 158 ± 9.2 | 15 |
| C | 30 | 165 ± 9.8 | 15 |
| D | 30 | 193 ± 10.3 | 15 |
| Control (Placebo) | — | 100 ± 10.5 | 15 |

TABLE 1-continued

| Compound | Dose mg/kg p.o. | Locomotor activity total movements/3 hours as percentage of the control | n |
|---|---|---|---|
| $\bar{x} \pm$ S.E. = 1986 $\pm$ 208.5 sec. | | | |

It is obvious from the above results that the compounds of the invention are capable to significantly increase the hyperactivity induced by L-DOPA and thus they provide an inportant improvement in diseases arising from a dopamine-deficiency.

(b) Inhibition of the neurotoxic action of 1--methyl-4-phenyl-1,2,3,6-tetrahydropyridine (MPTP)

In 1979 it was reported that MPTP caused the degeneration of the dopaminergic system in men and monkeys [G. C. Davis et al.: Psychiat. Res. 1, 249 (1979); R. S. Burns et al., Proc. Natl. Acad. Sci. (USA), 80, 4546 (1983)]; the selective dopaminergic system-damaging effect on mice of this compound was also shown [see e.g. H. Hallman et al.: Eur. J. Pharmacol. 97, 133 (1984); E. Pileblad et al.: Neuropharmacol. 24, 689 (1986)]. The selective dopaminergic system-damaging effect caused by MPTP on test animals can be considered to be a process analogous to the degenerative and hypofunctional diseases of the human dopaminergic system and thus it is a suitable model for investigating compounds useful for the therapeutical treatment of diseases connected with the pathological functioning of the dopaminergic system [A. J. Bradbury et al.: The Lancet 1985, 1444; H. Przuntek et al.; Life Sci. 37, 1195 (1985)].

For these investigations, male CFY mice (LATI, Gödöllo, Hungary) weighing 20-25 g were used. The compounds to be tested were homogenized in 1% Tween 80 solution and administered to the animals in a dose of 0.1 mmole/kg (in the route given in the Table) 1 hour before administzering MPTP. MPTP was freshly dissolved in physiological saline solution and subcutaneously given to the mice in a dose of 70 mg/kg. 72 to 96 hours after the administration of PMTP the animals were killed by decapitation, their brain was rapidly removed, cooled in an ice-cold physiological saline solution, the striatum was excised and refrigerated in dry ice.

The tissues (in a refrigerated condition) were weighed and homogenized in 1 ml of 0.4N perchloric acid solution containing 0.5% of $Na_2S_2O_5$, 0.25% of $Na_2EDTA$ and 100 ng of M-methyldopamine (internal standard for the determination of catecholamines) in an Ultra-Turrax equipment. The homogenate was centrifuged at 4° C. at 20,000 g for 10 minutes, then 0.8 ml of the supernatant was taken out. After adding 20 mg of activated aluminium oxide, the pH value of the solution was adjusted to 8 by adding 0.5M Tris solution and the tubes were shaken for 20 minutes. The aluminium oxide was settled, the supernatant was removed by suction and washed 3 times with 5 ml of distilled water each. The catecholamines adsorbed on the aluminium oxide were eluted with 1 ml of 0.05N perchloric acid. From a part of the eluate, dopamine was determined by using high pressure liquid chromatography by means of electrochemical detection (Labor MIM Oe-320 pump, 4×150 mm Nucleosil 5 C-18 analytical column and 4×20 mm Nucleosil 5 C-18 supplementary column; electrochemical detector fitted with a glassy-carbon working electrode and an Ag/AgCl$_2$ reference electrode; Eltron potentiostat, LKB 2110 2-channel recorder; with an oxidation potential of 600 mV and as mobile phase 0.1M $NaH_2PO_4$, 1 mM $Na_2EDTA$, 1 mM octanesulfonic acid containing 8.5% of acetonitrile; flow rate 1 ml/minute).

A decrease by 50 to 60% in the striatum dopamine level can be achieved by using the above method. The protection against the dopamine decrease induced by MPTP was calculated as follows:

$$\% \text{ inhibition} = \frac{(\text{treated with the compound} + \textit{MPTP}) - (\text{treated with } \textit{MPTP})}{(\text{control}) - (\text{treated with } \textit{MPTP})} \times 100$$

Trihexyphenidyl hydrochloride in a 10 mg/kg intraperitoneal dose was used as reference drug. This dose is lower than 0.1 mmole/kg but the animals perished by a dose higher than 10 mg/kg.

The results are summarized in Table 2.

TABLE 2

| Compound | Dose mmole/kg | Route of administration | Inhibition of the dopamine decrease induced by MPTP % | n |
|---|---|---|---|---|
| E | 0.1 | p.o. | 100 | 7 |
| F | 0.1 | i.p. | 85 | 7 |
| G | 0.1 | p.o. | 59 | 7 |
| H | 0.1 | p.o. | 61 | 7 |
| Trihexyphenidyl HCl | | i.p. | 7 | 7 |

It is obvious from the data of Table 2 that, when administered orally and/or intraperitoneally to the animals before the treatment with MPTP, the compounds of the general formula (I) are capable to inhibit in a high degree or completely the neurotoxic dopamine-depleting action of MPTP. In addition, the compounds of the general formula (I) possess an advantageously low toxicity. Thus, the novel compounds of the invention represent a valuable therapeutical tool for influencing clinical cases, wherein a dopaminergic hypofunction exists as a consequence of the degeneration of the dopaminergic system or for other reasons.

According to the invention, the compounds of the general formula (I) are prepared by (a) reacting a compound of the general formula (II),

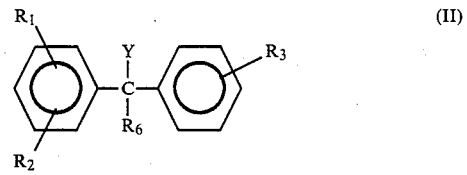

wherein $R_1$, $R_2$, $R_3$ and $R_6$ are as defined above and Y means halogen or a hydroxyl group or an OM group, wherein M stands for an alkali metal or an MgHlg group, wherein Hlg represents halogen, with a piperazine derivative of the general formula (III),

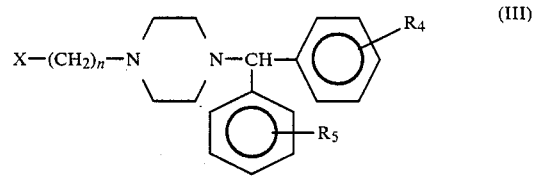

wherein R4, R5 and n are as defined above and X stands for halogen or a hydroxyl group or an OM' group, wherein M' means an alkali metal, with the provisos that:
(1) X stands for a hydroxyl group or for an OM' group, wherein M' means an alkali metal, preferably lithium, potassium or sodium, when Y represents halogen; or
(2) X stands for a hydroxyl group or a halogen atom when Y represents a hydroxyl group; or
(3) X stands for a halogen atom when Y means an OM group, wherein M is as defined above, or (b) reacting a compound of the general formula (IV),

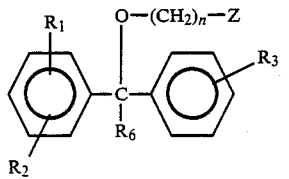

wherein $R_1$, $R_2$, $R_3$, $R_6$ and n are as defined above and Z stands for an alkylsulfonyloxy or arylsulfonyloxy group or a halogen atom, with a benzhydrylpiperazine derivative of the general formula (V),

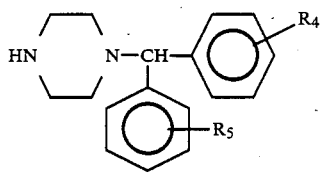

wherein R4 and R5 are as defined above, or
(c) reacting a compound of the general formula (VI),

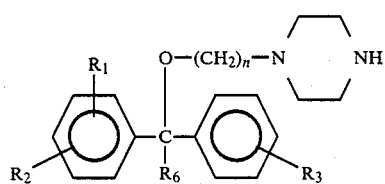

wherein $R_1$, $R_2$, $R_3$, $R_6$ and n are as defined above, with a benzhydryl halide of the general formula (VII),

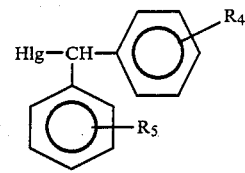

wherein R4, R5 and Hlg are as defined above, or
(d) reducing a compound of the general formula (VIII),

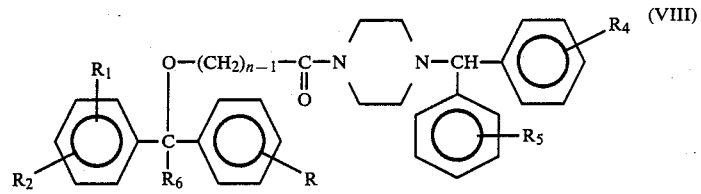

wherein $R_1$, $R_2$, $R_4$, $R_4$, $R_5$, $R_6$ and n are as defined above, and, if desired, transforming a thus-obtained product prepared by using any one of processes (a) to (d) to an acid addition salt with an organic or inorganic acid or to a quaternary ammonium salt with a quaternizing agent or, if desired, transforming a product obtained in the form of an acid addition salt or a quaternaary ammonium salt to the corresponding free base and/or, if desired, transforming a free base to its acid addition salt or quaternary ammonium salt.

The starting materials are known compounds or can be prepared by using processes known from the literature.

The compounds of the general formula (II), wherein Y stands for a hydroxyl group or a MgHlg group, wherin Hlg stands for halogen, may be synthetized e.g. by reacting the appropriate carbonyl compounds with Grignard reagents [see e.g.: M. S. Kharasch et al.: Grignard Reactions of Nonmetallic Substances, Ed. Prentice-Hall Inc., pp. 138–143 (1954)]. The alkoxides of the general formula (II) can be obtained e.g. by reacting the appropriate alcohols with an alkali metal, alkali metal hydride or alkali metal amide [see e.g. Houben-Weyl: Methoden der Organischen Chemie VI/2, pp. 6–34 (1963)].

The benzhydryl halides of the general formulae (II) and (VII) can be prepared e.g. by using the method of K. E. Hamlin et al. [J. Am. Chem. Soc. 71, 2731 (1949] or R. Baltzly et al. [J. Org. Chem. 14, 775 (1949)].

The alcohols and halides of the general formula (III) can be synthetized e.g. according to the Belgian patent specification No. 523,899 (CA 53, 18071 i) by reacting 1-(2-hydroxyethyl)piperazine or 1-(3-hydroxypropyl)-piperazine and then treating the thus-obtained alcohols with thionyl chloride. The alkoxides of the general formula (III) can be obtained as described above.

The compounds of the general formula (IV) can be synthetized e.g. according to the method of Sugasawa et al. [Org. Synth. 33, 11 (1953)]. These compounds can be prepared also by reacting the appropriate alcohols with an alkylsulfonyl halide such as methanesulfonyl chloride or with an arylsulfonyl halide such as 4-methylbenzenesulfonyl chloride.

The monosubstituted piperazines of the general formulae (V) and (VI) can be prepared by reacting an excess of piperazine with a halide compound of the general formula (VII) or (IV), respectively. This method is described e.g. in the U.S. Pat. No. 3,178,422 (CA 63, 4313 e).

The acid amides of the general formula (VIII) can be prepared e.g. by reacting the alkoxides of the general formula (II) with piperazine derivatives of the general formula (IX),

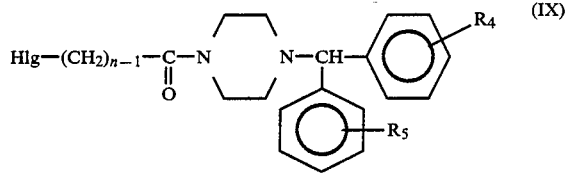

wherein R$_4$, R$_5$, n and Hlg are as defined above, as described above in process (a).

The compounds of the general formula (IX) can be obtained by the acylation of benzhydrylpiperazine derivatives of the general formula (V). This acylation can be accomplished by using e.g. chloroacetyl chloride or 3-bromopropionyl chloride in an inert organic solvent in the presence of an acid binding agent. This method is described e.g. in the U.S. Pat. No. 3,041,341 (CA 57, 13778d).

According to a preferred embodiment of process (a) of the invention, a compound of the general formula (II), wherein R$_1$, R$_2$, R$_3$ and R$_6$ are as defined above and Y stands for an OM group, wherein M is as defined above, is reacted with a piperazine derivative of the general formula (III), wherein R$_4$, R$_5$ and n are as defined above and X means a halogen atom preferably chlorine or bromine, in an organic solvent which is inert to the reaction. Suitable solvents are e.g.: aliphatic or alicyclic ethers such as ethyl ether, tetrahydrofuran or dioxane; aliphatic or aromatic hydrocarbons such as n-hexane, ligroin, benzene, toluene or xylene; as well as dimethylsulfoxide, hexamethylphosphoramide or the mixture of the above solvents. This reaction is preferably carried out under an inert gas such as nitrogen or argon.

When Y in the compound of the general formula (II) means a halogen atom, preferably chlorine or bromine and X in the employed compound of the general formula (III) stands for an OM' group, wherein M' represents an alkali metal, preferably lithium, potassium or sodium, then the reaction conditions are selected as described above.

When any one of Y and X stands for a hydroxyl group whereas the other means a halogen atom, then the reaction is preferably carried out in the presence of an inorganic or organic base which is suitable to bind the acid liberated in the reaction. Useful bases are the alkali metal carbonates or tertiary organic bases such as pyridine or triethylamine; however, an excess of the compound of the general formula (III) may also be used as an acid binding agent. This reaction can be accomplished either in an inert organic solvent or without any solvent.

When both Y and X are hydroxyl groups, then the condensation is preferably carried out in the presence of organic or inorganic acids or their acid salts such as sulfuric acid, p-toluenesulfonic acid, sodium hydrogen sulfate or the like, commonly used for ether formation under atmospheric or reduced pressure while distilling out azeotropically the formed water. Suitable solvents are aliphatic or aromatic hydrocarbons, e.g. n-heptane, toluene, xylene; or aliphatic or alicyclic ethers such as di(n-butyl)ether or dioxane. Other solvents promoting the dissolution, e.g. lower aliphatic acid amides or their mixtures, may also be used.

According to process (b) of the invention, a compound of the general formula (IV), wherein the meaning of the substituents is the same as defined above, is reacted in the form of its mesylate, tosylate, bromide or chloride with a benzhydrylpiperazine of the general formula (V). This reaction is preferably accomplished in an inert organic solvent, in the presence of a base which is useful for binding the acid liberated in the reaction. Suitable solvents for this reaction are e.g.: hydrocarbons such as ligroin, benzene, toluene or xylene; halogenated hydrocarbons such as chloroform; ethers such as di(n-butyl) ether, dioxane; alcohols such as ethanol; esters such as ethyl acetate; acid amides such as dimethylformamide; ketones such as acetone or methyl isobutyl ketone; or the mixtures of the above solvents. Useful acid binding agents are e.g. inorganic or tertiary organic bases such as alkali metal carbonates, alkali metal hydroxides, triethylamine or pyridine; as well as an excess of the benzhydrylpiperazine of the general formula (V). When a tertiary organic base or an excess of the piperazine derivative of the general formula (V) is used for acid binding, then these substances may also serve as solvents. This reaction may be carried out between 20° C. and the boiling point of the solvent, optionally in the presence of a catalyst. Useful catalysts are alkali metal iodides.

According to process (c) of the invention, a monosubstituted piperazine of the general formula (VI) is reacted with a benzhydryl halide of the general formula (VII), preferably with a benzhydryl chloride or bromide under conditions described for process (b) above.

In a preferred embodiment of process (d) of the invention, an acid amide of the general formula (VIII) is reduced with an aluminium complex, e.g. with lithium aluminium hydride. This reduction is accomplished in an inert organic solvent such as aliphatic or cycloaliphatic ether, e.g. ethyl ether, tetrahydrofuran or the mixtures thereof under an inert gas, e.g. nitrogen or argon, whereafter the complex formed is hydrolyzed.

If desired, the compounds of the general formula (I) can be transformed to their pharmaceutically acceptable acid addition salts or quaternary ammonium salts in a known way. For the preparation of acid addition salts, inorganic and organic acids can be used, e.g.: hydrogen halides such as hydrogen chloride, hydrogen bromide and the like; sulfuric acid and phosphoric acid; formic, acetic, propionic, oxalic, glycollic, maleic, fumaric, succinic, tartaric, ascorbic, citric, malic, salicylic, lactic, benzoic, cinnamic, aspartic, glutamic, N-acetylaspartic or N-acetylglutamic acid; as well as alkanesulfonic acids such as methanesulfonic acid and arenesulfonic acids such as p-toluenesulfonic acid and the like.

The acid addition salts can be prepared e.g. in such a way that the appropriate acid is added to a solution containing the compound of the general formula (I) in an inert solvent, e.g. to the ethanolic solution thereof, then the thus-obtained salt is precipitated by adding preferably a water-immiscible organic solvent such as ethyl ether.

For preparation of the quaternary salts, a lower alkyl, alkenyl or benzyl halide or an alkyl sulfate may preferably be used. The quaternization is carried out in an organic solvent, suitably e.g. in acetone, acetonitrile, ethanol or in a mixture thereof at a temperature between room temperature and the boiling point of the solvent. The thus-formed quaternary salt is isolated e.g. by filtration and, if desired, purified by recrystallization.

The compounds of the invention are transformed to pharmaceutical compositions. These compositions can be administered through oral, rectal and/or parenteral route. For oral administration, the composition can be prepared in the form of tablets, dragées or capsules. For the preparation of oral compositions, e.g. lactose or starch can be used as vehicle. Suitable binding or granulating agents are e.g. gelatine, sodium carboxymethylcellulose, methylcellulose, polyvinylpyrrolidone or starch gum. As disintegrating agents, particularly potato starch or microcrystalline cellulose can be added, but ultraamylopectin or formaldehyde-casein is also useful. Talc, collodial silicic acid, stearin as well as calcium and magnesium stearate or the like can be used as anti-adhesive and sliding agents.

Tablets can be prepared e.g. by wet granulation and subsequent compression. The mixture containing the active ingredients and vehicles and optionally a part of the disintegrating agent is granulated together with an aqueous, ethanolic or aqueous-ethanolic solution of the binding agents in an appropriate equipment, then the granulate is dried. Thereafter, the other disintegrating, sliding and anti-adhesive additives are mixed to the dried granulate and the mixture is compressed to tablets. Optionally the tablet is provided with a dissecting groove. The tablets can also be prepared by the direct compression of the mixture containing the active ingredient together with the needed additives. If desired, the tablets can be transformed to dragées by using the protective, flavouring and dyeing agents such as sugar, cellulose derivatives (methyl- or ethyl-cellulose or sodium carboxymethylcellculose), polyvinylpyrrolidone, calcium phosphate, calcium carbonate, food dyes, aromatizing agents, iron oxide pigments and the like which are commonly used in the pharmaceutical industry. For the preparation of capsules, the mixture of the active ingredients with the additivies is filled into a capsule.

For rectal administration, the composition is prepared in the form of a suppository. In addition to the active ingredient, the suppository also contains a vehicle base material, the so-called "adeps pro suppositorio". As vehicles, vegetable fats such as hardened vegetable oils and the triglycerides of $C_{12-18}$ fatty acids, preferably vehicles with the trade mark Witepsol ® can be used. The active ingredient is homogeneously dispersed in the molten vehicle mass and then the suppositories are prepared by moulding.

For parenteral administration, the composition is prepared in the form of an injectable solution. For the preparation of injectable solutions, the active ingredients are dissolved in distilled water and/or various organic solvents, e.g. glycol ethers, optionally in the presence of solubilizing agents such as polyoxyethylene sorbitan monolaurate, monooleate or monostearate (Tween 20, Tween 60 and Tween 80, respectively). In addition, the injectable solution contains also various additives such as preservatives, e.g. benzyl alcohol, methyl or propyl 4-hydroxybenzoate, benzalkonium chloride, phenylmercury borate and the like; as well as antioxidants, e.g. ascorbic acid, tocopherol, sodium pyrosulfate and optionally complex forming agents such as an ethylenediamine tetraacetate salt for binding the metal traces, as well as buffers for adjusting the pH value and optionally a local anaesthetizing agent, e.g. lidocaine. The injectable solution containing the active ingredient of the invention is filtered before filling into the ampoule and sterilized after filling.

The daily doses depend upon the condition of the patient and the disease to be treated and are in general between 5 and 200 mg for adults in the case of oral administration.

The invention also relates to a method for treating diseases arising from a decrease in the dopamine level, i.e. from a hypofunction of the dopaminergic system. This process comprises the use of a therapeutically effective amount of an active ingredient of the general formula (I) or a pharmaceutically acceptable acid addition or quaternary ammonium salt thereof to a subject in need of such treatment.

The invention is illustrated in detail by the aid of the following non-limiting Examples.

EXAMPLE 1

Preparation of 1-[2-[bis(4-fluorophenyl)-methoxy]ethyl]-4-(diphenylmethyl)piperazine A suspension containing 6.6 g of 4α'-difluorobenzhydrol and 0.9 g of a 80% oily sodium hydride dispersion in 26.5 ml anhydrous toluene is refluxed under argon gas for 15 minutes while stirring, then a solution of 9.5 of 4-diphenylmethyl-1-(21-chloroethyl)piperazine in 30 ml of anhydrous toluene is dropwise added and the thus-obtained reaction mixture is refluxed for additional 2 hours. After cooling down, water is added and the phases are separated. The toluence solution is washed with water, dried over anhydrous potassium carbonate and evaporated under reduced pressure. The residue is purified on a Kieselgel column by using chloroform as eluant. The residue obtained after evaporation of the appropriate fraction is recrystallized from ethanol to give the amide compound, m.p.: 112°–113° C.

Analysis: Calculated for $C_{32}H_{32}F_2N_2O$ (base) C 77.08; H 6.47; F 7.62; N 5.62%; found C 77.12; H 6.55; F 7.58; N 5.67%.

In order to precipitate the hydrochloride, an ethereal hydrogen chloride solution is added to the solution of the base in anhydrous ether up to a pH value of 2.5 to 3. The crystalline precipitate is filtered, washed and dried to give the dihydrochloride of the aimed base, m.p.: 185°–187° C.

EXAMPLE 2

Preparation of 1-[3-[1-(2,5-dimethylphenyl)-1-phenylpropoxy]propyl]-4-(diphenylmethyl)piperazine 2′,5′-Dimethylpropiophenone dissolved in 25 ml of anhydrous ether is dropped to 20 ml of an 1.5 molar ethereal phenylmagnesium bromide solution under nitrogen gas while stirring, then the reaction mixture is refluxed for 1 hour. Thereafter, a solution containing 9.8 g of 1-(3-chloropropyl)-4-dimethylphenylpiperazine in 50 ml of anhydrous xylene is dropwise added and after distilling off the ether, the reaction mixture is refluxed for additional 3 hours. After cooling, the mixture is poured into water, the organic phase is separated, washed with water and extracted with an aqueous hydrochloric acid solution. The acid extract is alkalized by adding aqueous ammonium hydroxide solution and extracted with ether. The ethereal solution is dried over anhydrous magnesium sulfate and evaporated. The residue is purified on a Kieselgel column by using a mixture of chloroform and methanol as eluant. After recrystallization from n-hexane, the base melts at 108°–110° C.

Analysis: Calculated for $C_{37}H_{44}N_2O$ (base) C 83.41; H 8.33; N 3.00%; found C 81.60; H 8.51; N 3.11%.

For obtaining the maleate, an ethereal maleic acid solution is added to the ethereal solution of the base. The precipitate is filtered and dried to give the di(hydrogen maleate), m.p.: 138°–140° C.

EXAMPLE 3

Preparation of 1-[3-(diphenylmethoxy)propyl]-4-[(2-chlorophenyl)-(4-fluorophenyl)methyl]piperazine A mixture containing 7.4 g of benzhydryl bromide and 21.8 g of 4-[(2-chlorophenyl)-(4-fluorophenyl)methyl]-1-(3-hydroxypropyl)piperazine is heated at 160° to 170° C. under nitrogen gas for 30 minutes, then cooled to 90° to 100° C. and poured into water. The aqueous phase is extracted with benzene, washed with water, the benzene solution is dried over anhydrous potassium carbonate and then evaporated under reduced pressure. The residue is purified by chromatography on a Kieselgel column by using a 4:1 mixture of benzene and chloroform as eluant. The thus-obtained product is recrystallized from n-hexane to give the aimed product, m.p.: 98°–99° C.

Analysis: Calculated for $C_{33}H_{34}ClFN_2O$ (base) C 74.91; H 6.48; Cl 6.70; F 3.59; N 5.29%; found C 75.00; H 6.55; Cl 6.65; F 3.61 N 5.34%.

The dihydrochloride salt is obtained by adding ethereal hydrogen chloride solution to the base dissolved in anhydrous ether. The crystalline precipitate is filtered and dried, m.p.: 120°–123° C.

EXAMPLE 4

Preparation of 1-[3-[bis(4-fluorophenyl)methoxy]propyl]-4-(diphenylmethyl)piperazine A solution containing 10.4 g of 1-[3-[bis(4-fluorophenyl)methoxy]propyl]piperazine, 4.6 ml of triethylamine and 8.1 g of benzhydryl bromide in 100 ml of anhydrous xylene is refluxed for 8 hours and then cooled down. The mixture is washed with water, dried over anhydrous magnesium sulfate and evaporated under reduced pressure. The residue is recrystallized from n-hexane to give the aimed product, m.p.: 78°–79° C.

Analysis: Calculated for $C_{33}H_{34}F_2N_2O$ (base) C 77.31; H 6.69; F 7.41; N 5.47%; found C 77.53; H 6.58; F 7.43; N 5.33%.

The dihydrochloride of the base melts at 92°–94° C.

EXAMPLE 5

Preparation of 1-[3-(diphenylmethoxy)propyl]-4-[(4-fluorophenyl)-phenylmethyl]piperazine dihydrochloride A mixture containing 8.1 g of 1-[(4-fluorophenyl)-phenylmethyl]piperazine, 11.8 g of 3-(diphenylmethoxy)propyl chloride, 6.9 g of powdered anhydrous potassium carbonate and 1 g of potassium iodide in 200 ml of methyl isobutyl ketone is refluxed for 18 hours while stirring and then cooled down. After evaporation of the mixture, water and benzene are added to the residue. The organic phase is separated, washed with water, dried over anhydrous magnesium sulfate and filtered through an aluminium oxide layer. The filtrate is evaporated under reduced pressure, the residue is taken up in anhydrous ether and ethereal hydrogen chloride solution is added. The precipitate is filtered and dried to give the aimed dihydrochloride, m.p.: 162°–165° C.

The base, m.p. 59°–60° C., can be obtained by adding aqueous sodium hydroxide solution to the dihydrochloride salt.

Analysis: Calculated for $C_{33}H_{35}FN_2O$ (base) C 80.13; H 7.13; F 3.84; N 5.66%; found C 80.28; H 7.20; F 3.90; N 5.77%.

The following compounds are prepared analogously to the process described in the above Example.

(a) 1-[3-[bis(4-fluorophenyl)methoxy]propyl]-4-[(4-fluorophenyl)phenylmethyl]piperazine, m.p.: 70°–71° C., is prepared by reacting 3-[bis(4-fluorophenyl)methoxy]propyl tosylate with 1-[(4-fluorophenyl)-phenylmethyl]piperazine. The dihydrochloride, m.p.: 147°–150° C., is obtained by adding ethereal hydrogen chloride solution to the base dissolved in ether.

Analysis: Calculated for $C_{33}H_{33}F_3N_2O$ (base) C 74.69; H 6.27; F 10.74; N 5.28%; found C 74.77; H 6.20; F 10.90; N 5.43%.

(b) 1-[3-[(3-Trifluoromethylphenyl)-(4(-methoxyphenyl)methoxy]propyl]-4-[(3-trifluoromethylphenyl)-(4-methyoxyphenyl)methyl]piperazine dimaleate, m.p.: 92°–94° C., is prepared by reacting 3-[(3-trifluoromethylphenyl)-(4-methoxyphenyl)methoxy]propyl bromide with 1-[(3-trifluoromethylphenyl)-(4-methoxyphenyl)methyl]piperazine.

Analysis: Calculated for $C_{37}H_{38}F_6N_2O_3$ (base) C 66.06; H 5.69; F 16.95; N 4.16%; found C 66.28; H 5.75; F 17.14; N 4.30%.

EXAMPLE 6

Preparation of 1-[3-[bis(4-fluorophenyl)methoxy]propyl]-4-[bis(4-fluorophenyl)methyl]piperazine A solution of 11.3 g of 1-[3-[bis(4-fluorophenyl)methoxypropionyl]-4-[bis(4-fluorophenylmethyl)]piperazine in 150 ml of anhydrous ether is dropped to 40 ml of an 1.0 molar ethereal lithium aluminium hydride solution under nitrogen atmosphere, then the mixture is refluxed for 3 hours. After cooling down, the mixture is decomposed by adding aqueous sodium hydroxide solution, filtered, the ethereal phase is washed with water, dried over anhydrous magnesium sulfate and evaporated. After dissolving in benzene, the residue is filtered through an aluminium oxide layer, the filtrate is evaporated and the residue is recrystallized from n-hexane to give the aimed base, m.p.: 73°–74° C.

The crystalline dihydrochloride of the base is obtained by adding ethereal hydrogen chloride solution to the ethanolic solution of the base. After filtration and drying, the dihydrochloride melts at 175°–176° C.

Analysis: Calculated for $C_{33}H_{32}F_4N_2O$ (base) C 72.24; H 5.88; F 13.85; N 5.11%; found C 72.07; H 6.00; F 13.88; N 5.20%.

EXAMPLE 7

Preparation of
1-[3-[(diphenylmethoxy)propyl]-4-[bis(fluorophenyl)-methyl]piperazine To a solution of 7.4 g of benzhydrol in 100 ml of xylene, 12.0 g of p-toluenesulfonic acid and 10.4 g of 1-[bis(4-fluorophenyl)methyl]-4-(3-hydroxypropyl)-piperazine dissolved in 50 ml of dimethylformamide are added under stirring, then the mixture heated to boiling and the water formed in the condensation reaction is continuously removed by azeotropic distillation. Then, the mixture is cooled down and the base is liberated with dilute aqueous ammonium hydroxide solution. The organic phase is separated, washed with water, dried over anhydrous sodium sulfate and evaporated under reduced pressure. The residue is purified by chromatography on a Kieselgel column by using a 5:1 mixture of benzene and chloroform as eluant. The product obtained after evaporating the appropriate fractions is recrystallized from n-hexane to give the aimed base, m.p.: 68°–60° C.

Analysis: Calculated for $C_{33}H_{34}F_2N_2O$ (base) C 77.31; H 6.69; F 7.41; N 5.47%; found C 77.53; H 6.65; F 7.48; N 5.60%.

The dihydrochloride melts at 166°–168° C.

EXAMPLE 8

Preparation of
1-[3-[bis(4-fluorophenyl)methoxy[propyl[-4-[(2-chlorophenyl)-(4-fluorophenyl)methyl]piperazine A suspension containing 10.9 g of 1-(3-hydroxypropyl)-4-[(2-chlorophenyl)-(4-fluorophenyl)methyl]-piperazine and 1.2 g of a 60% oily sodium hydride dispersion in 50 ml of anhydrous xylene is refluxed under argon gas for 30 minutes while stirring, then 8.6 g of 4,4'-difluorobenzhydryl chloride dissolved in 50 ml of anhydrous xylene are dropwise added. The mixture is refluxed for 6 hours, then cooled down and water is added. After separation, the organic phase is washed with water, dried over anhydrous magnesium sulfate and evaporated under reduced pressure. The residue is chromatographed on a Kieselgel column by using a 5:1 mixture of benzene and chloroform as eluant. The appropriate fractions are combined and evaporated under reduced pressure. After dissolving the residue in anhydrous ether, the dihydrochloride is precipitated by adding ethereal hydrogen chloride solution. The dihydrochloride of the aimed compound melts at 118°–120° C.

The base is liberated from the dihydrochloride with aqueous ammonium hydroxide solution. After recrystallization from n-hexane, the base melts at 91°–92° C.

By treating an ethereal solution of the base with an ethereal solution of methanesulfonic acid, the dimethanesulfonate salt of the base is obtained, m.p.: 110°–112° C.

Analysis: Calculated for $C_{33}H_{32}ClF_3N_2O$ (base) C 70.41; H 5.71; Cl 6.27; F 10.09; N 4.96%; found C 70.31; H 5.68; Cl 6.39; F 10.27; N 5.18%.

EXAMPLE 9

Preparation of
1-[2-[bis(4-fluorophenyl)methoxy]ethyl]-4-[bis(4-fluorophenyl)methyl]piperazine A mixture containing 12.7 g of 2-[bis(4-fluorophenyl)methoxy]ethyl chloride, 8.6 g of 1-[bis(4-fluorophenyl)methyl]piperazine, 6.2 g of powdered anhydrous potassium carbonate and 0.5 g of potassium iodide in 90 ml of methyl isobutyl ketone is refluxed for 20 hours while stirring. After cooling down, the mixture is evaporated under reduced pressure and water and ethyl ether are added to the residue. The ethereal phase is washed with water, dried over anhydrous magnesium sulfate and evaporated. The crude product is purified on a Kieselgel column by using a 2:1 mixture of benzene and chloroform as eluant. The appropriate fractions are combined, evaporated and the residue is recrystallized from ethanol to give the aimed compound, m.p.: 87°–88° C.

The base can be transformed to the dihydrochloride by adding an ethereal hydrogen chloride solution. The precipitate is filtered and dried, m.p.: 198°–200° C.

Analysis: Calculated for $C_{32}H_{30}F_4N_2O$ (base) C 71.89; H 5.66; F 14.22; N 5.24%; found C 72.00; H 5.51; F 14.40; N 5.25%.

EXAMPLE 10

The compounds of the invention can be formulated e.g. to pharmaceutical compositions described hereinafter.

Preparation of tablets 50 g of active ingredient, 92 g of lactose, 40 g of potato starch, 4 g of polyvinylpirrolidone, 6 g of talc, 1 g of magnesium stearate, 1 g of colloidal silicon dioxide (Aerosil) and 6 g of ultraamylopectin are mixed, granulated as wet and compressed to tablets each of which weighes 200 mg and contains 50 mg of the active ingredient which is 1-[2-[bis(4-fluorophenyl)methoxy]ethyl]-4-(diphenylmethyl)piperazine dihydrochloride.

Preparation of dragées

The tablets prepared as described above are covered in a known way with a coat consisting of sugar and talc, then the dragées are polished by using a mixture of bee wax and carnauba wax.

Each dragée weighes 250 mg.

Preparation of a suspension

The components of 100 ml of suspension are as follows:

| | |
|---|---|
| Active ingredient | 1.0 g |
| Sodium hydroxide | 0.26 g |
| Citric acid | 0.30 g |
| Nipagin (methyl 4-hydroxybenzoate) | 0.10 g |
| Carbopol 940 (polyacrylic acid) | 0.30 g |
| Ethanol (96%) | 1.00 g |
| Raspberry flavour | 0.60 g |
| Sorbitol (70% aqueous solution) | 71.00 g |
| Distilled water for injecvtion purpose q.s. ad | 100 ml |

Carbopol is added in little portions to the solution containing nipagin and citric acid in 20 ml of distilled water under vigorous stirring, then the solution is left to stand for 10 to 12 hours. Thereafter, the above-given amount of sodium hydroxide dissolved in 1 ml of distilled water is added, sorbitol is mixed in, finally the ethanolic solution of the raspberry flavour is added by stirring. The active ingredient is added to the vehicle in little portions, then the mixture is transformed to a suspension by using an immersed homogenizer. Finally, the suspension is filled up to 100 ml with distilled water and the thus-obtained suspension syrup is passed through a colloid mill.

The active ingredient is 1-[2-[bis(4-fluorophenyl)methoxy]ethyl]-4-(diphenylmethyl)piperazine.

We claim:

1. A benzhydrylipiperazine of the formula (I),

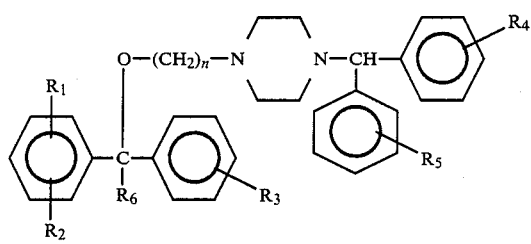

wherein $R_1$, $R_2$, $R_3$, $R_4$ and $R_5$ are the same or different and stand for hydrogen or halogen, or a trihalomethyl, $C_{1-4}$ alkyl or $C_{1-4}$ alkoxy group;

$R_6$ means hydrogen or a $C_{1-4}$ alkyl group; and n is 2 or 3, pharmaceutically acceptable acid addition and quaternary ammonium salts thereof.

2. A benzhydrylpiperazine selected from the group consisting of

1-[2-[bis(4-fluorophenyl)methoxy]ethyl]-4-diphenylmethylpiperazine,

1-[3-[bis(4-fluorophenyl)methoxy]propyl]-4-[(4-fluorophenyl)phenylmethyl]piperazine, and pharmaceutically acceptable acid addition and quaternary ammonium salts thereof.

3. A pharmaceutical composition for treating diseases arising from a decrease in dopamine level comprising, as active ingredient, an effective amount of the benzhydrylpiperazine of claim 1, or a pharmaceutically acceptable acid addition or quaternary ammonium salt thereof in admixture with carriers and/or additives commonly used in the pharmaceutical industry.

4. A method of treating mammals (including man) suffering from diseases arising from a decrease in the dopamine level, which comprises administering a therapeutically effective amount of a benzhydrylpiperazine of the formula (I),

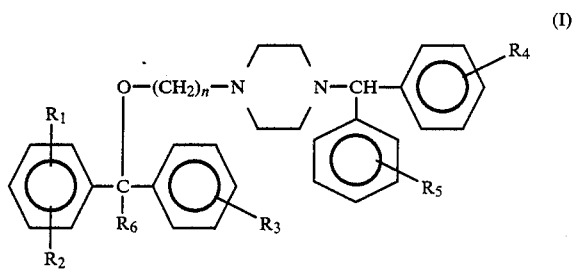

wherein $R_1$, $R_2$, $R_3$, $R_4$ and $R_5$ are the same or different and stand for hydrogen or halogen, or a trihalomethyl, $C_{1-4}$ alkyl or $C_{1-4}$ alkoxy group;

$R_6$ means hydrogen or a $C_{1-4}$ alkyl group; and n is 2 or 3, or a pharmaceutically acceptable acid addition or quaternary ammonium salt thereof, to a subject in need of such treatment.

5. The method of claim 4, wherein said benzhydrylpiperazine is selected from the group consisting of 1-[3-[bis(4-fluorophenyl)methoxy]propyl]-4-[bis(4-fluorophenyl)methyl]piperazine, 1-[3-](4-methoxyphenyl)-(3-trifluoromethylphenyl)methoxy]-propyl]-4-[4-methoxyphenyl)-(3-trifluoro-methyl-phenyl)methyl]piperazine, 1-[3-[bis(4-fluorophenyl)methoxy]propyl]-4-[(2-chlorophenyl)-(4-fluorophenyl)methyl]piperazine, 1-[3-(diphenylmethoxy)propyl]-4-[2-chlorophenyl)-(4-fluorophenyl)methyl]piperazine, 1-[2-[bis(4-fluorophenyl)methoxy]ethyl]-4-diphenylmethylpiperazine, 1-[3-[bis(4-fluorophenyl)methoxy]propyl]-4-[(4-fluorophenyl)phenylmethyl]piperazine, 1-[3-diphenylmethoxy)propyl]-4-[bis(4-fluorophenyl)-methyl]piperazine, and 1-[3-diphenylmethoxy)propyl]-4-[(4-fluorophenyl)-phenylmethyl]piperazine.

* * * * *